US 9,242,252 B2

(12) United States Patent
Eberle et al.

(10) Patent No.: US 9,242,252 B2
(45) Date of Patent: Jan. 26, 2016

(54) CASSETTE AND SYSTEM COMPONENT INSERTABLE INTO A CENTRIFUGE IN COOPERATION WITH THE CASSETTE

(75) Inventors: Klaus-Günter Eberle, Tuttlingen (DE); Roland Biset, Leuven (BE); Wilfried Mertens, Leuven (BE)

(73) Assignees: Terumo BCT, Inc., Lakewood, CO (US); Andreas Hettich GMBH & CO. KG, Tuttlingen (DE)

( * ) Notice: Subject to any disclaimer, the term of this patent is extended or adjusted under 35 U.S.C. 154(b) by 827 days.

(21) Appl. No.: 13/574,464

(22) PCT Filed: Jan. 5, 2011

(86) PCT No.: PCT/EP2011/050093
§ 371 (c)(1),
(2), (4) Date: Nov. 6, 2012

(87) PCT Pub. No.: WO2011/083119
PCT Pub. Date: Jul. 14, 2011

(65) Prior Publication Data
US 2013/0072368 A1 Mar. 21, 2013

(30) Foreign Application Priority Data
Jan. 8, 2010 (DE) .......................... 10 2010 000 753

(51) Int. Cl.
*B04B 5/04* (2006.01)
*A61M 1/36* (2006.01)
(Continued)

(52) U.S. Cl.
CPC ............ *B04B 5/0407* (2013.01); *A61M 1/3693* (2013.01); *B04B 5/0428* (2013.01); *B04B 7/00* (2013.01); *A61M 2205/12* (2013.01); *B04B 2005/0435* (2013.01); *F16K 7/063* (2013.01)

(58) Field of Classification Search
CPC .......... A61M 1/3693; A61M 2205/12; A61M 2205/128; A61M 39/284; B04B 5/0428; B04B 5/0407; B04B 7/00; B04B 7/02; B04B 2005/0435; B04B 2007/025; F16K 7/063
See application file for complete search history.

(56) References Cited

U.S. PATENT DOCUMENTS 5,456,845 A 10/1995 Nishimura et al.
5,543,062 A 8/1996 Nishimura
(Continued)

FOREIGN PATENT DOCUMENTS

DE 196 22 050 A1 5/1996
DE 100 65 283 A1 12/2000
(Continued)

OTHER PUBLICATIONS

International Search Report for International Application No. PCT/EP2011/050093; Date of Mailing: May 10, 2011.
(Continued)

*Primary Examiner* — Timothy Cleveland
(74) *Attorney, Agent, or Firm* — John R. Merlking

(57) ABSTRACT

The invention pertains to a cassette (2) comprising a product conveying path (1, 1a, 1b) and a shut-off device (19a, 19b) integrated into the cassette for interrupting a product flow. The shut-off device is arranged at a rim of the cassette such that the shut-off device (19a, 19b) can be directly operated manually and/or mechanically. The product-conveying path (1, 1a, 1b) leads through the shut-off device (19a, 19b). The cassette consists of a lower part (5) and an upper part (7) which are connectable to each other by connecting means (9, 11, 13, 15).

19 Claims, 8 Drawing Sheets

(51) Int. Cl.
  *B04B 7/00*   (2006.01)
  *F16K 7/06*   (2006.01)

(56) References Cited

U.S. PATENT DOCUMENTS

| | | |
|---|---|---|
| 5,734,464 A | 3/1998 | Gibbs |
| 5,795,317 A | 8/1998 | Brierton et al. |
| 6,234,989 B1 | 5/2001 | Brierton et al. |
| 6,361,518 B1 | 3/2002 | Brierton et al. |
| 7,166,217 B2 | 1/2007 | Holmes et al. |
| 7,194,087 B2 | 3/2007 | Luginbill et al. |
| 7,981,019 B2 | 7/2011 | Holmes et al. |
| 2002/0085957 A1 | 7/2002 | Moore et al. |
| 2003/0176267 A1 | 9/2003 | Eberle |
| 2004/0026341 A1 | 2/2004 | Hogberg et al. |
| 2008/0220959 A1 | 9/2008 | Holmes et al. |
| 2010/0170858 A1 | 7/2010 | Eberle et al. |
| 2011/0053201 A1 | 3/2011 | Eberle et al. |

FOREIGN PATENT DOCUMENTS

| | | |
|---|---|---|
| DE | 11 2004 000 569 T5 | 3/2006 |
| DE | 103 16 598 B4 | 5/2008 |
| DE | 10 2007 000 309 A1 | 12/2008 |
| DE | 10 2007 000 310 A1 | 12/2008 |
| DE | 10 2007 000308 A1 | 12/2008 |
| EP | 0499891 A1 | 8/1992 |
| EP | 0616816 A2 | 9/1994 |
| EP | 1351772 B1 | 12/2001 |
| EP | 1512464 A2 | 3/2005 |
| EP | 1 557 187 A1 | 7/2005 |
| GB | 2174149 A | 10/1986 |
| WO | 02053292 A1 | 7/2002 |
| WO | 03089027 A2 | 10/2003 |
| WO | 2004069310 A2 | 8/2004 |
| WO | 2007024550 | 3/2007 |
| WO | 2010061863 A1 | 6/2010 |

OTHER PUBLICATIONS

Written Opinion for International Application No. PCT/EP2011/050093; Date of Mailing: May 10, 2011.

Millipore Corp.: MulitiScreen Assay System, Centrifuge Alignment Frame, User Guide.

International Search Report for International Application No. PCT/EP2011/050094; Date of Mailing: May 2, 2011.

International Search Report dated Sep. 25, 2008 for PCT/EP2008/056923.

International Search Report dated Oct. 14, 2008 for PCT/EP2008/056925.

International Search Report dated Sep. 25, 2008 for PCT/EP2008/056926.

19b 191b   192b

19b

IV-IV

CASSETTE AND SYSTEM COMPONENT INSERTABLE INTO A CENTRIFUGE IN COOPERATION WITH THE CASSETTE

TECHNICAL FIELD

The invention relates to a cassette used as cover for accommodating blood bags for a cartridge of a centrifuge for separating blood components, and a system component insertable into such a centrifuge in cooperation with the cassette.

BRIEF DESCRIPTION OF RELATED ART

In transfusion medicine, the so-called blood component therapy has established itself since the beginning of the nineties. This means that, instead of a whole blood conserve, only those blood components required by the individual patient are administered to said patient. This separate administering of the individual blood components makes it possible that one single blood conserve is sufficient to optimally help an average of 1.8 patients.

The essential blood components are the red blood cells in the so-called erythrocyte concentrate, which are transfused in order to maintain the oxygen supply after severe loss of blood, the blood platelets in the thrombocyte concentrate, which are administered in cases of coagulation disturbances (haemophilia), and the blood plasma, which is administered in cases of coagulation disturbances and volume deficits.

Apart therefrom, blood plasma is an essential basic component for the production of many medicaments.

The separation of the individual blood components, which is defined as cell separation/isolation, is known to be effected by treating the blood in a centrifuge. By means of centrifuging, the individual blood components are separated from each other, and can then be separately filled into the respective containers for further use.

Documents DE 10 2007 000 308 A1, DE 10 2007 000 309 A1 and DE 10 2007 000 310 A1 already reveal a cartridge for use in a centrifuge for separating blood components and a respective centrifuge as well as a respective method. According to these documents, a cartridge comprises an intermediate wall and a cover. The intermediate wall separates a blood bag area disposed radially inside from a product area disposed radially outside. In an installation position of the cartridge, the cover is located above the blood bag area. The cover is connected to the intermediate wall pivotally at one point, and detachably at a second point. In this way, the blood bag area is freely accessible by a lateral turning away of the cover. For loading the cartridge with a blood bag, the cover is opened, a blood bag and a product bag are inserted into the respective chambers, and a connecting tube is inserted along a product conveying path. Moreover, photosensitive sensors are arranged along the product conveying path and are used to establish the composition of the product while the product is obtained; and, when a specific composition is reached, measures are taken for terminating the obtaining of the product. However, loading of the cartridge may only be effected manually, which renders it time- and cost-consuming. Besides, there is the possibility that the product is destroyed upon a faulty insertion of the connecting tube, since the sensors do not react timely.

Therefore, the known means need to be improved such that, on the one hand, faulty loading is avoided and, on the other hand, time is saved.

BRIEF SUMMARY

According to the invention, a cassette comprising a product conveying path and a shut-off device for interrupting a product flow are provided. The shut-off device is integrated into the cassette, and it is arranged at a rim of the cassette such that the shut-off device can be directly operated manually and/or mechanically. The product-conveying path leads through the shut-off device. The cassette comprises a lower part and an upper part which are connected to each other by snap elements or other means. Other means in terms of the invention may e.g. be screw joints and/or rivet joints, or bonded joints.

Preferably, the shut-off device can be provided in the form of two tube clamps that can be operated separately from each other.

Moreover, the shut-off device can be integrated either only into the lower part, or only into the upper part.

Preferably, the product-conveying path can be provided in the form of a passage, and a tube can be disposed in the product-conveying path. This is advantageous insofar as a tube laid along the product-conveying path remains reliably positioned, since it is excluded that the tube drops out of the product-conveying path when the cassette is handled. When assembling the cassette, the tube is inserted into the product-conveying path before the lower part and the upper part of the cassette are connected to each other.

Preferably, the cassette can comprise connecting means for being connected to a cartridge for accommodating the cassette, said cartridge being adapted to be accommodated in the centrifuge or in the system component arranged in the centrifuge. This constitutes an advantage insofar as, besides the tube, the cassette may also comprise a blood bag attached thereto and a product bag also attached thereto; compared to the prior art, this allows a quicker and more reliable loading of the cartridge.

Preferably, the cassette can comprise a positioning means that is engageable with a counter-piece on a centrifuge or a system component arranged in a centrifuge such that a section of the product-conveying path is aligned with a section of the centrifuge or the system component arranged in the centrifuge. In particular, the section of the product-conveying path and/or tube arranged directly adjacent to the positioning means can be exactly positioned to be directly adjacent to the counter piece.

This is advantageous because the system component may include sensors preferably arranged at the counter piece, and adapted to detect a composition of the product in the product-conveying path and/or tube. Depending on the composition of the product, the sensors can then output signals to a microprocessor monitoring and controlling further processes. In particular, due to the positioning means, it is ensured that an axis of the sensors substantially intersects a central axis of the product conveying path at a right angle.

The cassette according to the invention can be inserted into the system component. The system component is provided for arrangement in a centrifuge having a rotor rotatable around a hub for separating blood components. The system component can be integrated into the rotor, or can be freely inserted or removed from the same. The system component comprises an operating means used for operating a shut-off device of the cassette.

Preferably, the operating means can be provided in the form of an arrangement of levers. The operating means can have a centrally arranged lever whose ends can be directly or indirectly operated individually—i.e. independently of each other. If the end is operated directly, it has a longer stroke than if it is operated indirectly.

Besides, the operating means can have a short lever designed to act, when operated, on an opening means as well as on a closing means of the shut-off device of the cassette. Thus, the opening as well as the closing of the shut-off device is advantageously possible by the operation of the short lever.

To this end, the short lever is advantageously provided in the form of an L-shape and is rotatably supported. In particular, the short lever can be supported such that, when operated, one leg acts on the closing means of the shut-off device via the long end of the long lever, and the second leg of the short lever simultaneously acts on the opening means. This is particularly possible when the one short leg is supported such that one end of the long lever is disposed between the opening means of the shut-off device and the leg of the short lever.

When the short lever is operated, it then turns around the point on which it is supported. The one leg acts on the end of the long lever, said end being displaced by this effect in the direction of the closing means of the shut-off device. Simultaneously, the second leg of the short lever acts on the opening means of the shut-off device.

If the shut-off device is provided in the form of a tube clamp which is in a closed state, it is opened by the operation of the short lever. However, since the end of the long lever is simultaneously moved in the direction of the opening means preferably designed as an opening arm, the tube clamp does not burst open abruptly, but is opened slowly and evenly. That is, the stroke of the end of the long lever is shorter with this indirect operation than with the direct operation.

Preferably, the operating means can comprise a first piston operable manually and/or pneumatically and/or hydraulically and/or electrically. For closing the shut-off device, said piston directly acts on one of the ends of the long lever.

Besides, the system component can comprise a second piston operable manually and/or pneumatically and/or hydraulically and/or electrically, which, for opening the shut-off device, directly acts on a leg of the short lever and, via said one leg, indirectly on one of the ends of the long lever. Since the short lever is advantageously provided in an L-shape and rotatably, the second leg of the short lever directly acts on the opening means of the shut-off device.

Preferably, the cassette and the system component can be used in a centrifuge having a rotor rotatable around a hub for separating blood components. The system component is accommodated in the rotor, or integrated into the same. Moreover, a cartridge can be incorporated into the system component, and this cartridge can be provided with a cassette loaded with a blood bag and a product bag. The cassette is used as cover for a blood bag area of the cartridge.

The use of a cassette according to the invention and the system component according to the invention allows to obtain one or also plural blood products, such as plasma, erythrocytes, or thrombocytes. This may be obtained particularly in that a microprocessor can be provided in the system component to be used for controlling and monitoring the product extraction process.

Then, by means of the microprocessor, particularly the detection results of the sensors can be processed and the operations of the shut-off devices can be carried out accordingly. Advantageously, the microprocessor in the system component can furthermore be connected to another microprocessor accommodated in the rotor of the centrifuge, said microprocessor being adapted to carry out the control and the monitoring of the entire product extraction process.

As mentioned before, cassettes with the already inserted tube and two or more bags (one blood bag and at least one product bag) attached to the tube can be supplied to a user in the form of a kit. Thus, after a blood collecting process, the cassette comprising the tube and the bags can be inserted into a system component of a centrifuge, or directly into the centrifuge to perform a centrifugation process in which the blood in the one bag is separated and at least one of the separated blood components is transferred into the second bag.

After this centrifugation process has been completed, it is merely necessary to replace the cassette present in the centrifuge by a new one and to subject the old cassette to further processing. In this respect it is noted that, in general, any number of cassettes can be subjected to the centrifugation process. Preferably a number of six cassettes is processed simultaneously in the centrifuge.

Since the tubes and bags are replaced together with their related cassette, a remarkable reduction of dead time is achieved.

BRIEF DESCRIPTION OF THE DRAWINGS

Further advantages of the invention can be seen from the description of a currently preferred embodiment and the Figures attached. Referring to the Figures.

DETAILED DESCRIPTION

Figure 1:
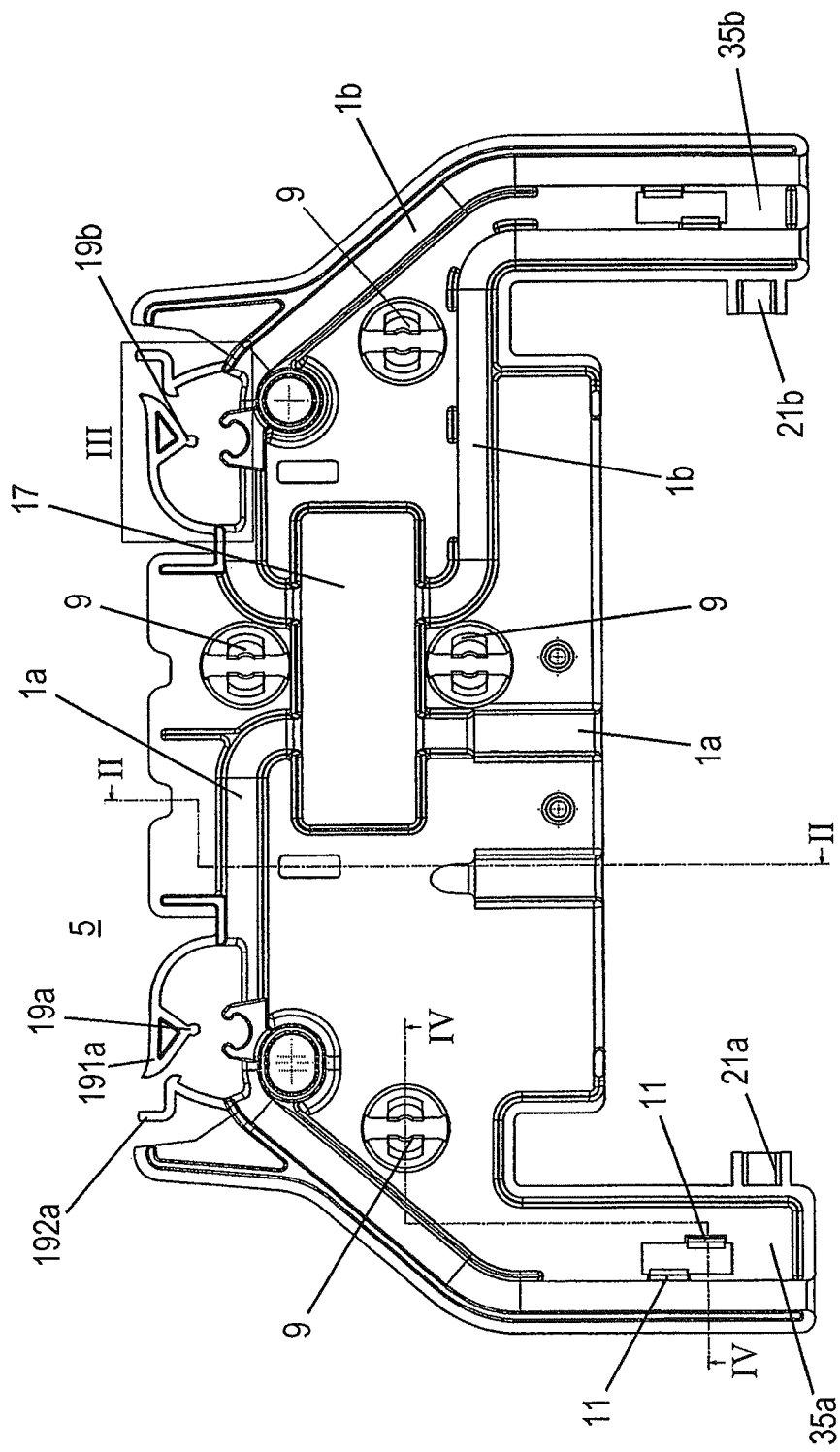
FIG. 1 shows a top view of a lower part of a cassette according to the invention.
Figure 2:
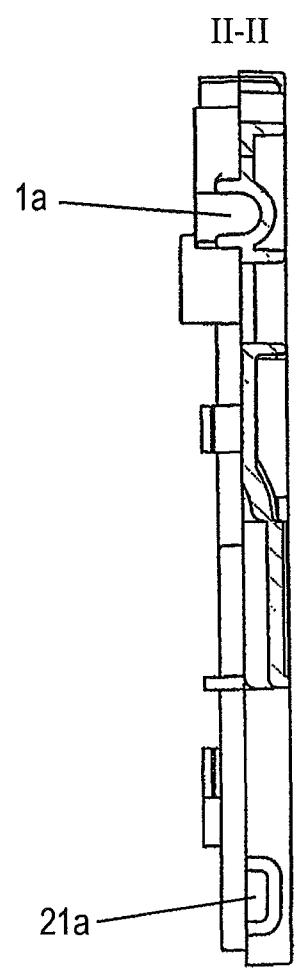
FIG. 2 shows a sectional view along a line II-II in FIG. 1.
Figure 3A:
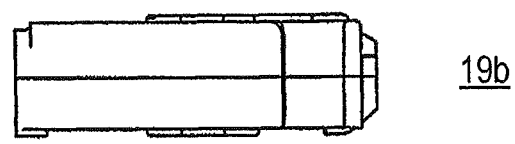
FIGS. 3a and 3b show a top view and a view of a detail III from FIG. 1, respectively.
Figure 3B:
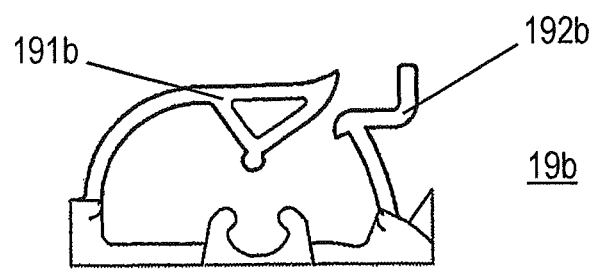
Figure 4:
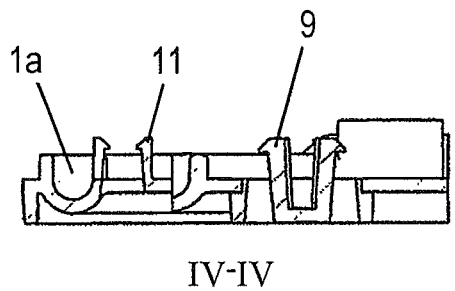
FIG. 4 shows a sectional view along a line IV-IV in FIG. 1.
Figure 5:
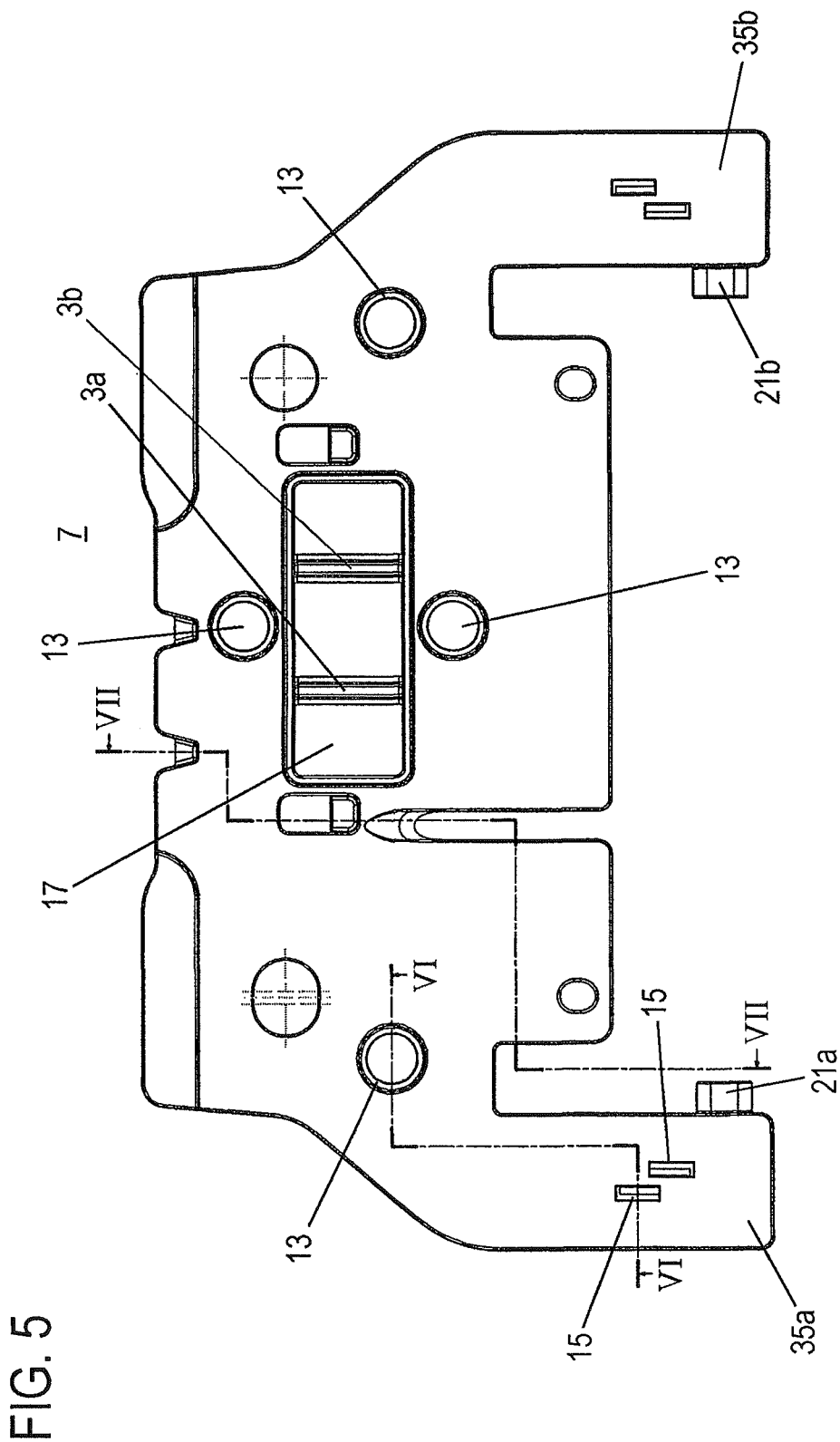
FIG. 5 shows a top view of an upper part of a cassette according to the invention.
Figure 6:
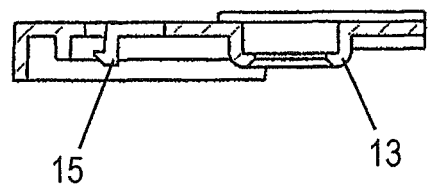
FIG. 6 shows a sectional view along a line VI-VI in FIG. 5.
Figure 7:
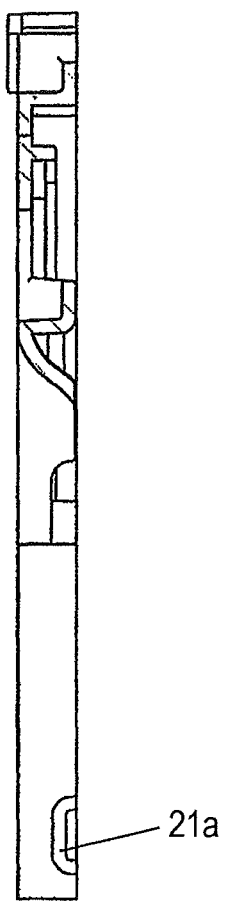
FIG. 7 shows a sectional view along a line VII-VII in FIG. 5.
Figure 8:
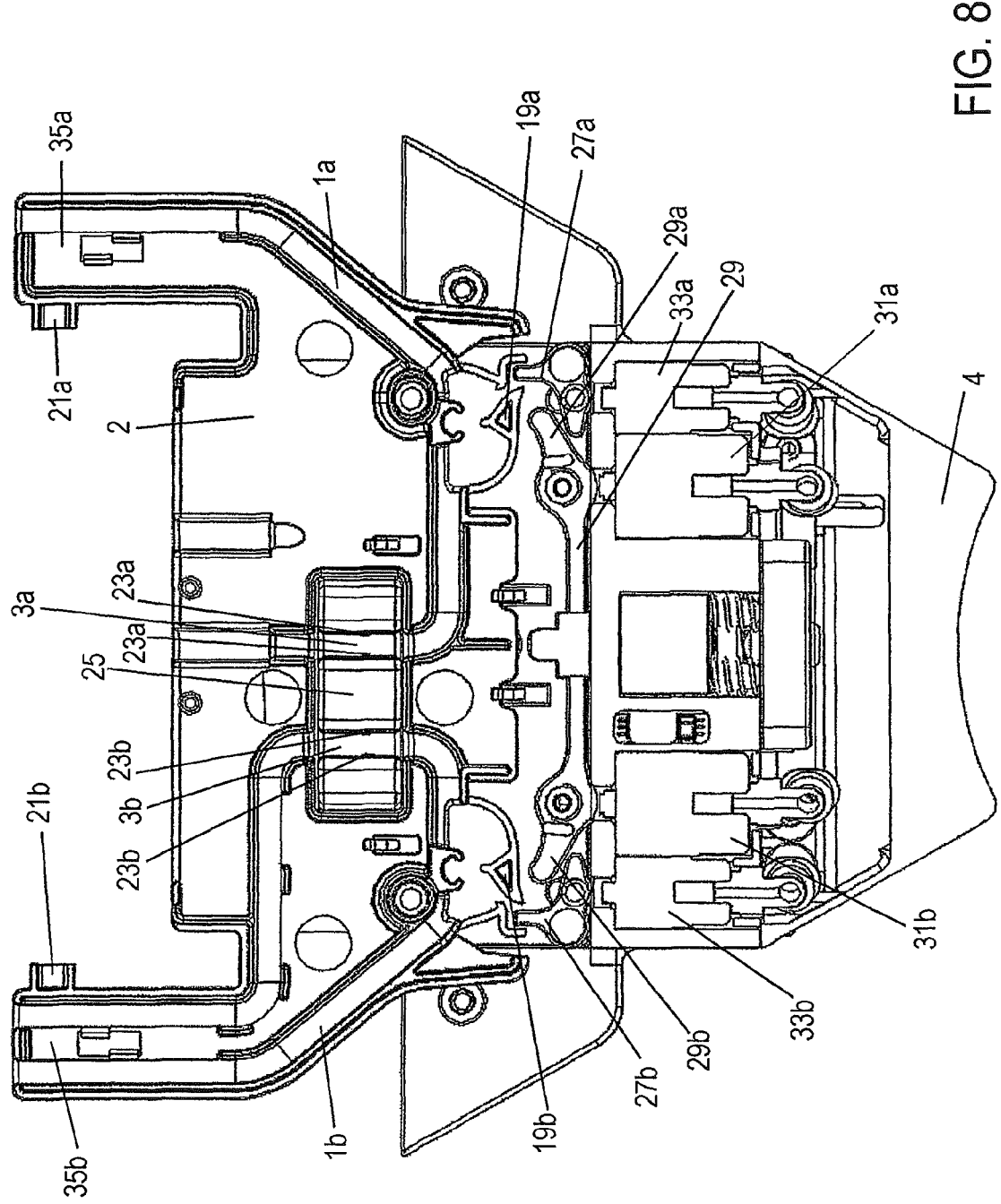
FIG. 8 shows a view of a cassette according to the invention, said cassette being provided in a system component according to the invention.

A currently preferred embodiment of the invention is described by means of FIGS. 1 to 8.

A cassette 2 according to the embodiment is composed of a lower part 5 and an upper part 7, which are connected to each other by means of snap elements 9 and 13, and 11 and 15, respectively. The upper part is made of a transparent material. Besides, as can be seen from the Figures, the cassette 2 approximately shows the form of a rectangle having two arms 35a, 35b.

The lower part 5 as well as the upper part 7 of the cassette 2 comprises a window 17 in a central area of the rectangle. Moreover, in the upper part 7, two bars 3a, 3b are formed in the window 17, and are used as positioning means according to the invention. The bars 3a, 3b extend along a partial section of a product-conveying path 1.

In the lower part 5, a channel-type passage 1 is formed as product-conveying path 1 according to the invention. The passage 1 is divided into two sections 1a and 1b. At an edge of the lower part 5 opposite the arms 35a, 35b, two tube clamps 19a, 19b are integrated into the lower part 5.

A tube (not shown in the Figures) provided with a blood bag, a filter and a product bag is laid in the product-conveying path 1 such that the tube is conducted from the blood bag disposed between the arms 35a, 35b to the first section 1a, along the bar 3a, through the tube clamp 19a arranged in the first section 1a further to the arm 35a. The tube then emerges from the arm 35a, leads to the filter, and enters the second section 1b of the passage 1 via the second arm 35b. Then, the tube is led along the bar 3b, through the tube clamp 19b and again the arm 35b, in order to emerge from the same towards the product bag.

At each of its arms 35a, 35b, the cassette 2 comprises a projection 21a, 21b disposed inside, which is used to detachably fix the cassette to a non-represented cartridge similar to the one in documents DE 10 2007 000 308 A1, DE 10 2007 000 309 A1 and DE 10 2007 000 310 A1. The blood bag, the filter and the product bag are then accommodated in appropriate chambers of the cartridge. The cassette 2 replaces a cover in the said applications.

Together with the cassette 2, the loaded cartridge is inserted into a system component 4 that is arranged in a centrifuge. An elevation 25 in which two grooves are formed is provided in a section of the system component 4. Photosensitive sensors 23a, 23b are inserted into the inner walls of each groove.

If the cassette 2 is disposed in the system component 4, the elevation 25 is engaged in a form-fit connection with the window 17, and the bars 3a and 3b with the grooves formed in the elevation 25. The sections of the tube extending along the bars 3a, 3b are disposed directly below the bars 3a, 3b, whereby the contents of the tube can be exactly registered by the photosensitive sensors 23a, 23b. The first photosensitive sensor 23a is assigned to the first section 1a of the product-conveying path 1, whereas the second photosensitive sensor 23b is assigned to the second section 1b of the product-conveying path 1. The optical axes of the photosensitive sensors 23a and 23b substantially intersect the central axis of the product conveying path (the tube) at a right angle.

Since the tube does not have to be inserted into the cassette 2 any more, but the cassette is already delivered together with the readily laid tube including blood bag, filter and product bag, a faulty insertion of the tube or a displacement of the tube that would lead to a faulty registration by the sensors can be reliably excluded.

Thus, it is possible, due to the interaction of the cassette according to the invention with the system component, to obtain a blood product by means of the method disclosed in document DE 10 2007 000 309 A.

According to the embodiment, the rotor of the centrifuge is designed for six system components 4 having one cartridge each. After all cartridges loaded with cassettes 2 have been inserted, the centrifuge is started. By means of the centrifugal force, the desired separation of the blood components is effected. Since the "buffy coat" diluted by an additive solution is in the blood bag, the lighter components thereof will remain radially inside, whereas its heavier components, i.e. the red blood cells, collect outside.

In order to transport the desired blood component—according to the embodiment, these are the platelets (thrombocytes)—in high quality, i.e. without the admixture of other blood cells, from the blood bag, the separation of the components will be followed by a slight pressure being applied onto the blood bag by means of a pressure pad, so that, after the previously closed tube clamps 19a, 19b have been opened, the solution rich in platelets begins to rise into the tube disposed in the passage 1. The solution rich in platelets is led through the tube into the filter designed as a leukocyte filter, and is further conducted therethrough.

In the leukocyte filter, the undesired leukocytes, i.e. the white blood cells, are removed. Due to the arrangement of the tube with the filter, the filtration is effected against the centrifugal force. Thus, heavier blood components, such as unintentionally transported red blood cells, are trapped in a filter-inlet chamber positioned radially outside.

After having passed the leukocyte filter, the solution rich in platelets continues flowing through the tube laid in the second section 1b of the passage 1 into a product bag, in which it is collected. Preferably, the product bag is already formed as final storage bag for the product.

In order to remove any air that might be present in the filter, the flow speed is kept low for a certain volume quantity at the beginning of the product transfer, thereby enabling the filter to fill with the blood product reliably and completely. After the transfer of this specific volume quantity, the conveying speed for a specific second volume quantity is increased by means of an appropriate control of the pressure pad. While this second volume is transported, there is hardly any risk that red blood cells contaminate the blood product (here: the thrombocyte concentrate). Should this nevertheless happen, this small number of red blood cells are collected in the lower and outer area of the filter, due to the tube being guided from radially outside and below into the filter, and due to the effect of the centrifugal force.

After the second volume has been transferred, the first photosensor 23a is activated and the flow speed of the blood product in the tube is reduced.

When the first photosensor 23a detects a predetermined proportion of red blood cells in the thrombocyte-rich solution, it outputs a signal by means of which the flow speed is again reduced. Furthermore, the second photosensor 23b disposed behind the filter is activated.

During this phase, also a rather large number of red blood cells can enter the filter and even pass therethrough until the second photosensor 23b detects a predetermined proportion of red blood cells in the blood product and outputs a signal for terminating the cell separation process. By this signal, the tube clamps 19a, 19b are closed by operation of the ends 29a, 29b of a long lever 29 by means of pistons 31a, 31b, so that the red blood cells in the filter are reliably separated from the thrombocyte concentrate in the product bag.

As an alternative to the termination by the second photosensor 23b, the cell separation process can also be terminated after a certain period of time has elapsed after the activation of the second photosensor 23b.

In the embodiment, altogether six cartridges are provided in the centrifuge. The above-described control of the cell separation process in a cartridge 1 by means of a pressure pad, the opening and closing of the tube clamps 19a, 19b, and the process control by means of the two photosensors 23a, 23b enables a continued cell separation in the cartridges of the other system components, since the described process control takes place individually for every combination of cartridge and system component.

The control of the process is effected by a microprocessor provided in the system component, said microprocessor processing the detection/registration results of the sensors 23a, 23b and accordingly controlling the opening and closing of the tube clamps 19a, 19b by operating the levers 31a, 31b and 33a, 33b, respectively. Besides, the microprocessor is connected to a microprocessor arranged in the hub of the rotor of the centrifuge for controlling the centrifuge and monitoring the microprocessors in the individual system components.

When the above-mentioned process is carried out, a precise operation of the tube clamps 19a, 19b is required for ensuring an optimum yield while simultaneously avoiding a contamination of the product. For operating the tube clamps 19a and 19b integrated in the lower part 5 of the cassette 2, the invention provides, in the system component, an arrangement having a centrally arranged long lever 29 and L-shaped, short levers 27a, 27b arranged at the two ends 29a and 29b of the long lever 29. The ends 29a, 29b of the long lever are disposed between a leg of the short lever 27a, 27b and a closing arm 191 of the tube clamps 19a and 19b, respectively.

At its central section, the long lever 29 is fixed to the system component 4. The short levers 27a, 27b are pivotally supported around the intersection of the two legs of the "L". The entire lever arrangement is disposed along the edge of the cassette 2, on which the tube clamps 19a, 19b are arranged when the cassette is inserted in the system component.

Pistons 31a, 31b, 33a, 33b, which are suitably arranged in the system component 4, are used for operating the levers 27a, 27b and 29. The pistons 31a, 31b act directly on the respective end 29a, 29b of the long lever. The pistons 33a, 33b act directly on a leg of the short levers 27a and 27b, respectively, said leg being disposed between the pistons 33a and 33b and the respective ends 29a, 29b of the long lever 29.

Since the ends 29a, 29b of the long lever 29 are disposed directly opposite the closing arm 191 of the tube clamps 19a and 19b when the cassette is inserted, an operation of the piston 31a or 31b leads to the closing of the respective tube clamp 19a or 19b. Since, in turn, an operation of the pistons 33a, 33b acts on the one leg of the rotatably supported, short levers 27a and 27b, respectively, this operation leads to a twisting of the levers 27a and 27b, respectively. The leg disposed between the pistons 33a and 33b acts on the end 29a or 29b of the long lever 29, whereas the other leg of the short lever 27a or 27b acts on an opening arm 192 of the tube clamp 19a or 19b, thereby opening the same. The indirect operation of the ends 29a, 29b of the long lever serves to exclude that the tube clamp bursts open too suddenly or too wide, so that problems e.g. due to the tube clamps getting jammed can be avoided.

The invention has been described by means of a currently preferred embodiment. However, it is not restricted thereto in any way, but only defined by the scope of the claims attached.

The invention claimed is:

1. A system component for being arranged in a centrifuge having a rotor rotatable around a hub for separating blood components, wherein the system component comprises:
   an operating means formed by an arrangement of at least two levers adapted to operate a shut-off device of a cassette,
   wherein the operating means has a first centrally arranged lever having an end that can be directly moved by a first piston or indirectly moved by a second lever,
   wherein said end has a longer stroke if moved by said first piston than if moved by said second lever.

2. A system component according to claim 1, wherein said second lever is designed to act, when moved, directly on an opening means of the shut-off device of the cassette and indirectly on a closing means of the shut-off device of the cassette by moving said first lever to limit movement of said closing means.

3. A system component according to claim 2, wherein the second lever is provided in the form of an L-shape having two legs and is rotatably supported such that, when operated, a first leg acts on the closing means of the shut-off device via the end of the first lever, and a second leg of the second lever acts on the opening means.

4. A system component according to claim 3, wherein the first piston is operable manually or pneumatically or hydraulically or electrically.

5. A system component according to claim 4, wherein the operating means comprises a second piston operable manually or pneumatically or hydraulically or electrically, which, for opening the shut-off device, directly acts on a leg of the second lever and, via the leg, indirectly on the first lever.

6. A system component according to claim 1, wherein the first piston is operable manually or pneumatically or hydraulically or electrically.

7. A system component according to claim 2, wherein the first piston is operable manually or pneumatically or hydraulically or electrically, said piston directly acting on said end of said first lever for closing the shut-off device.

8. A system component according to claim 7, wherein the operating means comprises a second piston operable manually or pneumatically or hydraulically or electrically, which, for opening the shut-off device, directly acts on the second lever and indirectly on the first lever through said second lever.

9. A centrifuge comprising
   a rotor rotatable around a hub for separating blood components, and
   at least one system component accommodated in the rotor or integrated into the same,
   a cartridge accommodated in the system component and
   a cassette loaded with a blood bag and a product bag,
      wherein the cassette is used as cover for a blood bag area of the cartridge,
      wherein the system component comprises:
         an operating means formed by an arrangement of at least two levers adapted to operate a shut-off device of a cassette,
         wherein the operating means has a first centrally arranged lever having an end that can be directly moved by a first piston or indirectly moved by a second lever,
         wherein said end has a longer stroke if moved by said first piston than if moved by said second lever.

10. The centrifuge as in claim 9,
   wherein said second lever is designed to act, when moved, directly on an opening means of the shut-off device of the cassette and indirectly on a closing means of the shut-off device of the cassette by moving said first lever to limit movement of said closing means and
   wherein the second lever is provided in the form of an L-shape having two legs and is rotatably supported such that, when operated, a first leg acts on the closing means of the shut-off device via the end of the first lever, and a second leg of the second lever acts on the opening means.

11. The centrifuge as in claim 10, wherein the first piston is operable manually or pneumatically or hydraulically or electrically and
   wherein the operating means comprises a second piston operable manually or pneumatically or hydraulically or electrically.

12. The centrifuge as in claim 9 wherein the cassette is configured for gaining one or more blood products and wherein the cassette comprises:
   a product conveying path and the shut-off device integrated into the cassette for interrupting a product flow, said shut-off device being arranged at a rim of the cassette such that the shut-off device can be directly operated manually or mechanically,
   wherein the product-conveying path leads through the shut-off device, and
   wherein the cassette consists of a lower part and an upper part which are connectable to each other by connecting means.

13. The centrifuge as claim 12, wherein the shut-off device is provided in the form of two tube clamps that can be operated separately from each other.

14. The centrifuge as in claim 12, wherein the shut-off device is integrated into the lower part or into the upper part.

15. The centrifuge as in claim 12, wherein the product-conveying path is provided in the form of a passage being formed by connecting the lower part and the upper part between these parts.

16. The centrifuge as in claim 12, wherein a tube is disposed in the product conveying path.

17. The centrifuge as in claim 12, wherein the cassette comprises connecting means for being connected to a cartridge for accommodating the cassette, said cartridge being adapted to be accommodated in the centrifuge or in the system component arranged in the centrifuge.

18. The centrifuge as in claim 12, wherein the cassette comprises a positioning means that is engageable with a counter-piece on said centrifuge such that a section of the product-conveying path is aligned with a section of the centrifuge.

19. The centrifuge as in claim 12,
wherein the shut-off device is provided in the form of two tube clamps that can be operated separately from each other and
wherein the shut-off device is integrated into the lower part or into the upper part and
wherein the product-conveying path is provided in the form of a passage being formed by connecting the lower part and the upper part between these parts and
wherein a tube is disposed in the product-conveying path and
wherein the cassette comprises connecting means for being connected to a cartridge for accommodating the cassette, said cartridge being adapted to be accommodated in the centrifuge or in the system component arranged in the centrifuge and
wherein the cassette comprises a positioning means that is engageable with a counter-piece on said centrifuge such that a section of the product-conveying path is aligned with a section of the centrifuge.

* * * * *